United States Patent [19]

Hickok

[11] Patent Number: 4,528,773

[45] Date of Patent: Jul. 16, 1985

[54] METHOD FOR PRODUCING GENES CONFERRING RESISTANCE TO HERBICIDES, GROWTH REGULATORS OR OTHER CHEMICAL AGENTS IN VASCULAR PLANTS

[75] Inventor: Leslie G. Hickok, Knoxville, Tenn.

[73] Assignee: University of Tennessee Research Corporation, Knoxville, Tenn.

[21] Appl. No.: 530,219

[22] Filed: Sep. 8, 1983

[51] Int. Cl.³ .............................................. A01G 1/00
[52] U.S. Cl. ...................................................... 47/58
[58] Field of Search ............................................ 47/58

[56] References Cited

U.S. PATENT DOCUMENTS 4,443,971  4/1984  Chaleff .................................... 47/58

OTHER PUBLICATIONS

Genetic Control of Photomorphogenesis Isolation of Nonfilamentous Mutants After Gamma Irradiation of Petridium Aquilinum Spores, G. P. Howland and Emmit L. Boyd, Radiation Botany, 14, (1974), 281–285.
Production of Auxotrophic Mutants in Ferns, P. S. Carlson, Genet. Res., Camb., 14, (1969), 337–339.

*Primary Examiner*—Robert E. Bagwill
*Attorney, Agent, or Firm*—Luedeka & Neely

[57] ABSTRACT

A method for producing genes conferring resistance to herbicides, growth regulators or other chemical agents in vascular plants is disclosed. Mutagenized spores of ferns of the genus Ceratopteris are grown in the presence of a herbicide, growth regulator, or other chemical agent and resistant mutant gametophytes are selected. Self-fertilization in the selected mutant gametophytes yields homozygous diploid sporophytes which also exhibit resistance. The sporophytes grown to maturity yield mutant spores having identical haploid genotypes which are grown to confirm the existence of resistance to the herbicide, growth regulator, or other chemical agent. The method produces vascular plant genes conferring resistance to the herbicide, growth regulator or other chemical agent.

4 Claims, 1 Drawing Figure

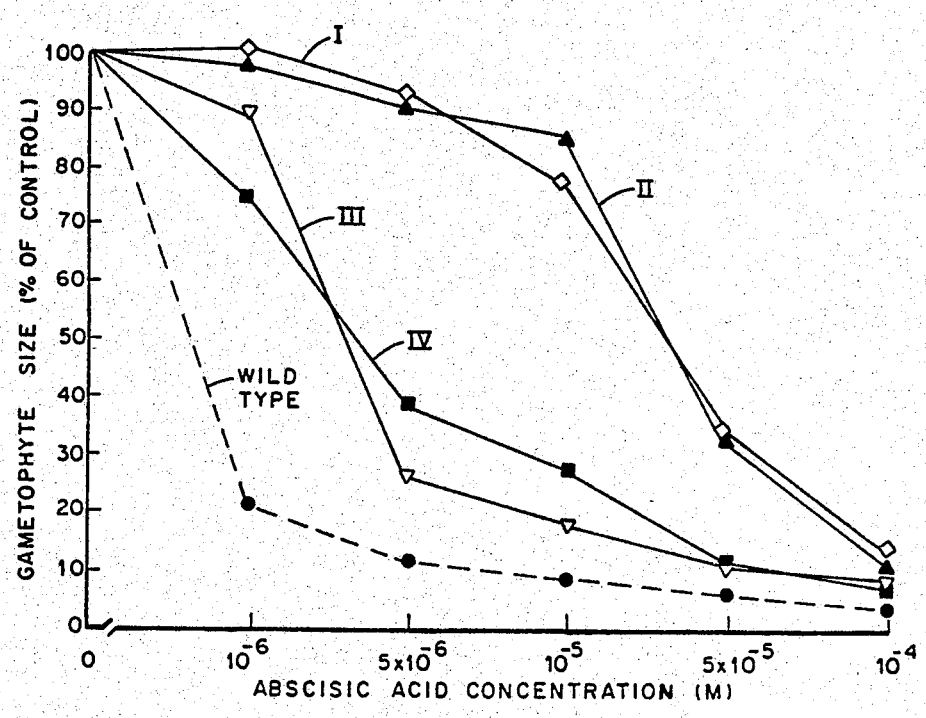

METHOD FOR PRODUCING GENES CONFERRING RESISTANCE TO HERBICIDES, GROWTH REGULATORS OR OTHER CHEMICAL AGENTS IN VASCULAR PLANTS

The present invention relates to genetic engineering in plants and more particularly relates to a method for producing genes conferring resistance to herbicides, growth regulators, or other chemical agents in vascular plants.

In order to develop new varieties of crop plants with increased capabilities by genetic engineering techniques, it is necessary to create a source of genes known to have beneficial properties such as resistance to herbicides, growth regulators, or other chemical agents. There have been difficulties in identifying and selecting such genes through standard plant genetic methodologies.

While the availability of genes suitable for transfer is limited, other techniques for the genetic engineering of plants have been developed. Vector construction, the production of a vehicle for transferring genetic information to recipient plants, and other techniques have been developed to the extent that genes may be transferred from one plant to another. Thus, for plant genetic engineering, methods are needed for the production of vascular plant genes that confer resistance to herbicides, growth regulators or other chemical agents.

Generally for vascular plants, existing mutation induction techniques and mutation screens for identifying mutant genes rely on diploid seeds and plants; that is, plants having two similar sets of chromosomes, each contributing to the genotype or total genetic material of the plant. The diploid state of these plants complicates the genetic aspects due to, for example, the formation of chimeras, the masking of recessive mutations in the heterozygous state, and the limited number of individuals available for screening. Although some of these limitations can be avoided by using plant cell and tissue culture techniques to provide a large population of cells to mutagenize and select from, the difficulties involving genetic and chromosomal instabilities and the inability to regenerate whole plants can complicate mutation screens that utilize cell and tissue cultures.

Therefore, the object of the present invention is to provide a simplified method for providing a source of resistance conferring genes for use in genetic engineering of vascular plants. Other objects and advantages of the invention will become known by reference to the following description and accompanying drawing in which:

The drawing is a chart graphically portraying the growth response to abscisic acid of four abscisic acidresistant mutants (I, II, III, IV) of EXAMPLE I.

I have discovered that the production of genes conferring resistance to herbicides, growth regulators, or other chemical agents can be accomplished by a method including exposing spores of a species of fern of the genus Ceratopteris to a mutagenizing agent. The mutagenized spores are grown to produce at least some mutant gametophytes on a growth supporting medium containing a selected concentration of a herbicide, growth regulator, or other chemical agent [hereinafter collectively referred to as a selection agent]. The gametophyte stage of the fern life cycle has only one set of chromosomes and thus is in the haploid state. Mutant gametophytes which exhibit resistance to the selection agent are isolated and are grown to maturity on a growth supporting medium. The isolated gametophytes, being bisexual, are caused to self-fertilize and to produce a sporophyte, the second stage of the fern life cycle. The mutant sporophyte is diploid and homozygous, that is, having two identical sets of chromosomes, since the sperm and egg were both contributed from the same haploid gametophyte. The mutant sporophyte is grown to maturity and produces mutant spores which are genetically identical. The mutant spores may be used to produce a supply of plant material as a source of genes which confer resistance to the selection agent in vascular plants.

Both the mutant sporophyte and the gametophytes grown from the mutant spores exhibit resistance to the selection agent. Leaves of the mutant sporophyte treated with the selection agent respond physiologically to show resistance such as by decreased chlorophyll loss compared to the wild type fern. Mutant gametophytes may be tested for resistance by sowing mutant spores in a growth supporting medium containing the selection agent to produce genetically identical mutant gametophytes. An increased growth rate in comparison to wild type ferns in the presence of the selection agent also confirms the existance of resistance to the selection agent.

The ferns of the genus Ceratopteris are classified within four species, *Ceratopteris thalictroides, Ceratopteris richardii, Ceratopteris pteridoides,* and *Ceratopteris cornuta.* All four species are homosporous and, thus, produce only one type of spore. As mentioned above, the life cycle of the Ceratopteris ferns consists of two independent and autotrophic generations, the haploid gametophyte stage and the diploid sporophyte stage. The first stage begins when the uninucleate spores germinate to produce haploid gametophytes. The gametophytes are nonvascular and photosynthetic. In the method of the present invention, the gametophytes may be grown in the presence of the selection agent to sufficient size to permit selection and isolation of mutant gametophytes within two to four weeks. The gametophytes of the ferns of the genus Ceratopteris, when grown to maturity, are bisexual, are less than 3 mm in diameter and contain antheridia and archegonia, the male and female sex organs, respectively. Fertilization in the gametophyte, either cross or self-fertilization, produces a diploid sporophyte. This second stage of the life cycle of Ceratopteris ferns is vascular and when grown to maturity again produces spores to again being the life cycle. Using the method of the present invention, an entire life cycle, spore to spore, is completed in four months.

The spores of the Ceratopteris ferns, are exposed to a mutagentic agent such as X-irradiation, gamma-irradiation, or chemical mutagens to cause mutagenesis. An exposure to the mutagenizing agent that results in few spore deaths and yields a small number of morphologically irregular gametophytes is preferred. Exposure is adjusted for the different species to achieve the desired result. Before mutagenesis, the spores preferably should be surface sterilized and materials and equipment should be in a sterile condition.

Mutants are grown from the mutagenized spores of the Ceratopteris ferns in a mineral nutrient medium containing a concentration of the selection agent. An agar-solidified mineral nutrient medium containing Parker's macronutrients and Thompson's micronutrients is used. The selection agent can be any appropriate growth regulator, herbicide, or the like, for example, abscisic acid or paraquat, or any chemical agent that affects plant growth, such as the base analog 5-flurodeoxyuridine, etc.

The concentration of the selection agent to be used in the method is determined by sowing non-mutagenized spores of the Ceratopteris fern in a mineral nutrient medium containing a range of concentrations of the selection agent. A concentration of the selection agent is chosen for the method of the invention which affects the growth or development of the gametophyte. Preferably, the concentration chosen is the lowest concentration of selection agent that uniformly and unambiguously supresses the growth or alters normal development.

The mutagenized spores are germinated and grown in the agar-solidified mineral nutrient medium containing the selection agent for a period of time sufficient to permit examination by the unaided eye or by a low power microscope, typically for a period of two to four weeks. The cultures are screened for the presence of mutant gametophytes that exhibit resistance to the selection agent. Resistance to the selection agent is shown typically by larger size but may also be indicated by morphological differences such as the presence or absence of sex organs. The selected gametophytes are treated as putative mutants.

The putative mutants of the Ceratopteris ferns are isolated by transferring them individually to a petri dish containing an agar-solidified mineral nutrient medium with or without the selection agent. The nutrient medium again contains Parker's macronutrients and Thompson's micronutrients. When the gametophytes are sexually mature, they are watered and are caused to self-fertilize and produce diploid homozygous sporophytes. Each sporophyte is cultured to a state of maturity and haploid spores are again produced which are referred to as M2 spores. The M2 spores from a mutant sporophyte are genetically identical.

When the selection agent is a herbicide that either directly or indirectly results in chlorophyll loss (bleaching), resistance is shown in the sporophyte by a decreased loss of chlorophyll in the mutants, compared to the wild type, when the selection agent is applied to the leaves of the sporophyte.

Resistance is also shown in the gametophyte generation. The M2 spores of the mutant Ceratopteris ferns are germinated and grown in the presence of the selection agent to produce mutant gametophytes that are genetically identical. The agar-solidified nutrient medium described above is again used. Resistance to the selection agent is shown by differences in growth of the mutant gametophytes in the presence of the selection agent compared to the wild type of the fern species in the presence of the selection agent.

The method of the present invention produces an essentially unlimited source of genetically identical vascular plants having resistance to the selection agent. Because the plants produced by the method may be vegetatively reproduced and controlled self and cross-fertilizations are easily performed, genetic characterization and confirmation of the mutants is greatly simplified. Thus, genes conferring resistance to the selection agent in vascular plants are produced and are made available for use in gene transfers.

The following are specific examples of a process employing features of the invention.

EXAMPLE I

The method is used with the species of fern *Ceratopteris richardii* and the selection agent is abscisic acid.

Spores are harvested from a mature sporophyte of the species *Ceratopteris richardii*. The harvested spores are placed in a 15 ml centrifuge tube, are soaked in tap water for 24 hours, and are surface sterilized with a 1.0% solution of sodium hypochlorite for a period of 3-5 minutes. The spores are rinsed twice with sterile distilled water. Centrifugation is used to remove water or the sodium hypochlorite solution in these procedures. The surface sterilized spores are placed in sterile water in glass petri dishes and are exposed to X-irradiation for 28 minutes at 400 R/minute. The irradiated spores are then sown in 100 mm×15 mm sterile petri dishes with approximately 500-700 spores per dish containing a sterile nutrient medium having an abscisic acid concentration of $10^{-4}M$. The nutrient medium is prepared by mixing the appropriate quantity of abscisic acid to result in a $10^{-4}M$ concentration with a solution containing Parker's macronutrients and Thompson's micronutrients as specified in the procedure in Klekowski, E. J., 1969, Reproductive Biology of the Pteridophyta. III. A Study of the Blecnaceae, Botanical Journal Linnean Society, 62:361-377. The medium is prepared as specified in the following table:

| Code | Parker's Macronutrients | (g)/(ml) |
|---|---|---|
| A | Ammonium nitrate, $NH_4NO_3$ | 2.5/100 |
| B | Potassium phosphate, $KH_2PO_4$ | 2.0/100 |
| C | Magnesium sulphate, $MgSO_4.7H_2O$ | 1.0/100 |
| D | Calcium chloride, $CaCl_2$ | 1.0/100 |

| Code | Thompson's Micronutrients | (g)/(l) |
|---|---|---|
| $1_t$ | Manganese sulphate | 0.022/1 |
| | Copper sulphate | 0.024/1 |
| | Zinc sulfate | 0.029/1 |
| | Boric acid | 0.186/1 |
| | Ammonium molybdate | 0.0035/1 |
| $11_t$ | Ferrous sulphate.$7H_2O$ | 2.5/1 |
| | Sodium EDTA | 3.7/1 |

Ingredients of growth medium:
1. 1 liter of distilled water
2. 10 g of agar
3. Macroelement stock solutions
   A   5 ml
   B   25 ml
   C   12 ml
   D   2 ml
4. Microelement stock solutions
   $1_t$   10 ml
   $11_t$   10 ml The petri dishes containing the nutrient medium and the spores are placed in individual plastic bags on flat culture decks in a culture room where the temperature is maintained at 25±2° C. and fluorescent light at 23 $W \cdot m^{-2}$ is provided by Sylvania cool-white 35 W tubes. The spores germinate and the gametophytes are grown for 21 days. The gametophyte cultures are screened for putative mutants by visually selecting gametophytes which are larger than most other gametophytes in the culture. As a result of the above treatment, 229 putative mutants are selected from a total number of 450,000 germinated spores.

The putative mutants are isolated by transferring each individually into a 60 mm×15 mm petri dish containing a nutrient medium with an abscisic acid concentration of $10^{-4}$M. The nutrient medium is prepared by the same method as for the nutrient medium used to germinate the irradiated spores. The mutant gametophytes are grown in a culture room at $25\pm2°$ C. and light at 23 W·m$^{-2}$ is provided by Sylvania cool-white 35 W tubes. After 15-20 days, the antheridia and archegonia of the mutant gametophytes are fully developed indicating sexual maturity. At this time, approximately 10 ml of sterile distilled water is added weekly using a sterile wash bottle until self-fertilization is effected and diploid homozygous sporophytes are produced.

The sporophytes are grown in the petri dishes containing the mineral nutrient medium with abscisic acid and added water for 15-20 days at the same temperature and light conditions. Then, the mutant sporophytes are transferred to 3-4 inch pots containing a soil mixture of 2 parts peat:1 part sand:1 part topsoil. The mutant-sporophytes are grown under greenhouse conditions for 60-80 days until the sporophytes are mature and spores are produced. Spores, referred to M2 spores, are then harvested. The M2 spores when germinated result in genetically identical mutant gametophytes which are resistant to abscisic acid.

The drawing graphically portrays the results of Example I for four of the 229 mutants, I, II, III and IV. The results were obtained by placing approximately 100 M2 spores of the abscisic acid-resistant mutants I, II, III and IV and approximately 100 spores of wild type *Ceratopteris richardii* in sterile 100 mm×15 mm petri dishes containing the same nutrient medium as has been previously described and various concentrations of abscisic acid as shown in the drawing. Control samples using approximately 100 of the M2 spores and the wild type spores are prepared in an identical manner without the abscisic acid. All samples are maintained at $25\pm2°$ C. and are provided with fluorescent light at 23 W·m$^{-2}$ by Sylvania cool-white 35 W tubes. The growth responses of the mutants and the wild type in the presence of abscisic acid are expressed as a percentage of growth by size over a fifteen-day period in comparison to the corresponding control without abscisic acid.

The growth responses to abscisic acid of four abscisic acid-resistant mutants (I, II, III and IV) are illustrated in the drawing. Two levels of resistance are evident. Mutants I and II differ greatly from the wild type in that little effect on size is evident until a concentration of $1\times10^{-5}$M abscisic or higher. Both mutants maintain greater than 90% of their growth potential at a concentration of $5\times10^{-6}$M while the wild type expresses less than 15% of its growth potential. Mutants III and IV show an intermediate level of resistance in terms of size. It is apparent that at least two classes of resistant mutants are produced from *Ceratopteris richardii* by the procedures of Example I.

EXAMPLE II

The method is used with the species of fern *Ceratopteris thalictroides* and the selection agent is abscisic acid.

Spores are harvested from a mature sporophyte of the species *Ceratopteris thalictroides*. The harvested spores are placed in a 15 ml centrifuge tube, are soaked in tap water for 24 hours, and are surface sterilized with a 1.0% solution of sodium hypochloride for a period of 3-5 minutes. The spores are rinsed with sterile distilled water. Certrifugation is used to remove water or sterilizing solution in these procedures. The surface sterilized spores are placed in sterile water in glass petri dishes and are exposed to X-irradiation for 38 minutes at 400 R/minutes. The irradiated spores are then sown in 100 mm×15 mm sterile petri dishes with approximately 500-700 spores per dish containing a sterile nutrient medium having an abscisic acid concentration of $10^{-4}$M. The nutrient medium is prepared as in Example I. The petri dishes containing the nutrient medium and the spores are placed in individual plastic bags on flat culture decks in a culture room where the temperature is maintained at $25\pm2°$ C. and fluorescent light at 23 W·m$^{-2}$ is provided by Sylvania cool-white 35 W tubes. The spores germinate and the gametophytes are grown for 21 days. The gametophytes are screened for putative mutants by visually selecting gametophytes which are larger than most other gametophytes in the culture. As a result of the above treatment, 139 putative mutants are selected from a total number of 150,000 germinated spores.

The putative mutants are isolated by transferring each individually into a 60 mm×15 mm petri dish containing a nutrient medium with no selection agent. The nutrient medium is prepared by the same method as for the nutrient medium used to germinate the irradiated spores. The mutant gametophytes are grown in a culture room at $25\pm2°$ C. and light is provided at 23 W·m$^{-2}$ by Sylvania cool-white 35 W tubes. After 15-20 days, the antheridia and archegonia of the mutant gametophytes are fully developed indicating sexual maturity. At this time, approximately 10 ml of sterile distilled water is added weekly using a sterile wash bottle until self-fertilization is effected and diploid homozygous sporophytes are produced.

The sporophytes are grown in the petri dishes containing the mineral nutrient medium and added water for 15-20 days at the same temperature and light conditions. Then, the mutant sporophytes are transferred to 3-4 inch pots containing a soil mixture of 2 parts peat:1 part sand:1 part topsoil. The mutant sporophytes are grown under greenhouse conditions for 60-80 days until the sporophytes are mature and spores are produced. Spores, referred to M2 spores, are then harvested. The M2 spores when germinated result in genetically identical mutant gametophytes which are resistant to abscisic acid.

The growth response to abscisic acid of two abscisic acid-resistant mutants (V, VI) was shown by placing approximately 100 M2 spores of the abscisic acid-resistant mutants V and VI and approximately 100 spores of wild type *Ceratopteris thalictroides* in sterile 100 mm×15 mm petri dishes containing the same nutrient medium as Example I and various concentrations of abscisic acid. Control samples using approximately 100 of the mutant spores and the wild type spores are prepared in an identical manner without the abscisic acid. All samples are maintained at $25\pm2°$ C. and are provided with fluorescent light at 23 W·m$^{-2}$ by Sylvania cool-white 35 W tubes.

The growth responses of the mutants V and VI to abscisic acid were apparent in sex organ (antheridia) differentiation at higher concentrations of abscisic acid. Mutant V averaged 12.5 antheridia per gametophyte at an abscisic acid concentration of $10^{-4}$M while antheridia averaged only 0.2 per gametophyte in the wild type at $5\times10^{-5}$M. Mutant VI showed an intermediate level of antheridia development with an average of 7.4 antheridia per gametophyte at $5\times10^{-5}$M. It is apparent that at least two types of resistant mutants are produced from *Ceratopteris thalictroides* by the procedures of Example II.

EXAMPLE III

The method is used with the species of fern *Ceratopteris richardii* and the selection agent is the herbicide paraquat (1,1'-dimethyl-4,4'-bipyridilium dichloride).

Spores are harvested from a mature sporophyte of the species *Ceratopteris richardii*. The harvested spores are placed in a 15 ml centrifuge tube, are soaked in tap water for 24 hours, and are surface sterilized with a 1.0% sodium hypochlorite solution for a period of 3–5 minutes. The spores are rinsed with sterile distilled water. Centrifugation is used to remove water or sterilizing solution in these procedures. The surface sterilized spores are placed in sterile water in glass petri dishes and are exposed to X-irradiation for 28 minutes at 400 R/minute. The irradiated spores are then sown in 100×15 mm. sterile petri dishes with approximately 500–700 spores per dish containing a sterile nutrient medium having a paraquat concentration of $5 \times 10^{-7}$M. The nutrient medium is prepared as in Example I. The petri dishes containing the nutrient medium and the spores are placed in individual plastic bags on flat culture decks in a culture room where the temperature is maintained at $25 \pm 2°$ C. and fluorescent light 23 W·m$^{-2}$ is provided by Sylvania cool-white 35 W tubes. The spores germinate and the gametophytes are grown for 21 days. The gametophytes are screened for putative mutants by visually selecting gametophytes which are larger than most other gametophytes in the culture. As a result of the above treatment, 80 putative mutants are selected from a total number of 200,000 germinated spores.

The putative mutants are isolated by transferring each individually into a 60 mm×15 mm petri dish containing a nutrient medium containing no selection agent. The nutrient medium is prepared by the same method as for the nutrient medium used to germinate the irradiated spores. The mutant gametophytes are grown in a culture room at $25 \pm 2°$ C. and light is provided at 23 W·m$^{-2}$ by Sylvania cool white 35 W tubes. After 15–20 days, the antheridia and archegonia of the mutant gametophytes are fully developed indicating sexual maturity. At this time, approximately 10 ml of sterile distilled water is added weekly using a sterile wash bottle until self-fertilization is effected and diploid homozygous sporophytes are produced.

The sporophytes are grown in the petri dishes containing the mineral nutrient medium and added water for 15–20 days at the same temperature and light conditions. Then, the mutant sporophytes are transferred to 3–4 inch pots containing a soil mixture of 2 parts peat:1 part sand:1 part topsoil. The mutant-sporophytes are grown under greenhouse conditions for 60–80 days until the sporophytes are mature and spores are produced. Spores, referred to M2 spores, are then harvested. The M2 spores when germinated result in genetically identical mutant gametophytes which are resistant to paraquat.

The confirmation of inherited resistance to paraquat is made in both the homozygous sporophytes that are produced from the putative mutant gametophytes and in the M2 generation of gametophytes. Resistance in the sporophytes is demonstrated by floating 0.1 g fresh weight of excised leaves of young sporophytes in a $10^{-6}$M solution of paraquat and monitoring the extent of chlorophyll loss over a 48 hour period in continuous light (23 W·m$^{-1}$). The results are given in the following table which indicates that resistance levels in the mutants range from over 2 to approximately 9 times the wild type:

| Sporophyte | O.D. at 650, μm | Chl. a + b (mg.) ($\times 10^{-2}$) | % of control |
|---|---|---|---|
| Water Control[a] | 1.006 | 13.99 | 100 |
| Wild type | 0.058 | 0.81 | 5.8 |
| Mutant A | 0.472 | 6.56 | 46.9 |
| Mutant B | 0.267 | 3.71 | 26.5 |
| Mutant C | 0.144 | 2.00 | 14.3 |

Chlorophyll loss in sporophyte leaves of wild type and paraquat-resistant mutants after 48 hour treatment with $10^{-6}$ M paraquat.

[a]Controls in plain water were run with leaves of the wild type and Mutant B values were averaged.

Gametophytes of the M2 generation are tested for resistance by sowing spores from three mutants (A,B,C) on the same medium with $5 \times 10^{-7}$M paraquat (the selection concentration). Techniques described in Examples I and II are utilized. These tests result in normal growth of gametophytes on paraquat at the selection concentration, indicating that resistance is maintained through the life cycle and expressed in the M2 generation.

EXAMPLE IV

The method is used with the species of fern *Ceratopteris richardii* and the selection agent is 5-flurodeoxyuridine.

Spores are harvested from a mature sporophyte of the species *Ceratopteris richardii*. The harvested spores are placed in a 15 ml centrifuge tube, are soaked in tap water for 24 hours, and are surface sterilized with a 1.0% sodium hypochlorite solution for a period of 3–5 minutes. The spores are rinsed with sterile distilled water. Centrifugation is used to remove water or sterilizing solution in these procedures. The surface sterilized spores are placed in sterile water in glass petri dishes and are exposed to X-irradiation for 28 minutes at 400 R/minute. The irradiated spores are then sown in 100 mm×15 mm sterile petri dishes with approximately 500–700 spores per dish containing a sterile nutrient medium having a 5-flurodeoxyuridine concentration of $5 \times 10^{-5}$M. The nutrient medium is prepared as in Example I. The petri dishes containing the nutrient medium and the spores are placed in individual plastic bags on flat culture decks in a culture room where the temperature is maintained at $25 \pm 2°$ C. and fluorescent light at 23 W·m$^{-2}$ is provided by Sylvania cool-white 35 W tubes. The spores germinate and the gametophytes are grown for 21 days. The gametophytes are screened for putative mutants by visually selecting gametophytes which are larger than most other gametophytes in the culture. As a result of the above treatment 195 putative mutants are selected from a total number of 400,000 germinated spores.

The putative mutants are isolated by transferring each individually into a 60 mm×15 mm petri dish containing a nutrient medium with a 5-flurodeoxyuridine concentration of $5 \times 10^{-5}$M. The nutrient medium is prepared by the same method as for nutrient medium used to germinate the irradiated spores. The mutant gametophytes are grown in a culture room at $25 \pm 2°$ C. and light at 25 W·m$^{-2}$ is provided by Sylvania cool-white 35 W tubes. After 15–20 days, the antheridia and archegonia of the mutant gametopohytes are fully developed indicating sexual maturity. At this time, approximately 10 ml of sterile distilled water is added weekly using a sterile wash bottle until self-fertilization is effected and diploid homozygous sporophytes are produced.

The sporophytes are grown in the petri dishes containing the mineral nutrient medium with 5-flurodeoxyuridine and added water for 15-20 days at the same temperature and light conditions. Then, the mutant sporophytes are transferred to 3-4 inch pots containing a soil mixture of 2 parts peat:1 part sand:1 part topsoil. The mutant-sporophytes are grown under greenhouse conditions 60-80 days until the sporophytes are mature and spores are produced. Spores, referred to M2 spores, are then harvested. The M2 spores when germinated result in genetically identical mutant gametophytes which are resistant to 5-flurodeoxyuridine.

The putative mutants exhibit resistance to 5-flurodeoxyuridine by continued vigorous growth in the medium containing 5-flurodeoxyuridine.

Results similar to the four examples described will be obtained with the other two Ceratopteris species, *Ceratopteris pteridoides*, and *Ceratopteris cornuta*. However, because these two species are relatively rare and are difficult to culture, use of *Ceratopteris thalictroides* and *Ceratopteris richardii* is preferred.

The method of the present invention produces mutant ferns of the genus Ceratopteris having resistance to herbicides, growth regulators or other chemical agents. Mutants of all four species of the genus Ceratopteris may be produced having resistance to a selection agent and large numbers of ferns genetically identical to a particular selected mutant may be produced. Thus, the method of the present invention provides genetically identical plants having resistance to the selection agent.

The present invention avoids problems associated with existing mutation induction techniques and mutation screens for vascular plants using diploid seeds and plants or cell and tissue cultures. Since the mutation occurs in the uninucleate hapoid spore, the identical genetic material is present in all resultant cells in the mutant gametophytes, thus, avoiding problems associated with the formation of chimeras. As opposed to cell and tissue culture techniques, the gametophytes represent intact photosynthetic plants. As such, the responses both the mutants and the wild types are fully representative of the responses expected in entire plants. The production of a homozygous sporophyte entirely eliminates the problems associated with the heterozygous diploid state such as the masking of recessive mutations. The mutants containing genes conferring resistance to the selection agent are thus positively identified and reproduced. The method of the present invention produces resistant putative mutants in as short a time period as 21 days. Spores of the mutants can be produced in approximately four months. Any desired number of plants genetically identical to a resistant mutant can be produced in a relatively short time period.

The method of the present invention therefore provides a simplified and expeditious method for providing a source of genes conferring resistance to herbicides, growth regulators or other chemical agents in vascular plants.

While preferred embodiments of the present invention have been shown and described, it will be understood that there is no intent to limit the invention by such disclosure, but rather, it is intended to cover all modification and alternate embodiments falling within the spirit and scope of the invention as defined in the appended claims.

What is claimed is:

1. A process for producing genes conferring resistance in vascular plants to a selection agent which comprises a herbicide, growth regulator or chemical agent affecting plant growth, comprising the steps of:
   (a) exposing spores of a fern of the genus Ceratopteris to a mutagenizing agent to mutagenize at least some of said spores;
   (b) growing said mutagenized spores to produce at least some mutant gametophytes in a growth supporting medium containing a selected concentration of the selection agent;
   (c) isolating mutant gametophytes exhibiting resistance to the selection agent;
   (d) growing said isolated mutant gametophytes to maturity on a growth-supporting medium;
   (e) causing said mutant gametophytes to self-fertilize and produce sporophytes;
   (f) growing said sporophytes to maturity and to produce mutant spores; and
   (g) employing said mutant spores from step (f) to produce a supply of plant material as a source of genes which confer resistance to said selection agent in vascular plants.

2. The process of claim 1 wherein spores exposed to said mutagenizing agent are of a fern selected from the group consisting of *Ceratopteris thalictroides* and *Ceratopteris richardii*.

3. The process of claim 1 wherein said mutagenizing agent is selected from the group consisting of X-rays and gamma rays.

4. The process of claim 3 wherein the selection agent is selected from the group consisting of abscisic acid, paraquat, and 5-flurodeoxyuridine.

* * * * *